United States Patent [19]

Gerhart

[11] Patent Number: 5,470,586
[45] Date of Patent: Nov. 28, 1995

[54] ANTIFOULING COATING AND METHOD FOR USING SAME

[75] Inventor: Donald J. Gerhart, Hillsborough, N.C.

[73] Assignee: Duke University, Durham, N.C.

[21] Appl. No.: 226,287

[22] Filed: Apr. 11, 1994

Related U.S. Application Data

[62] Division of Ser. No. 961,159, Oct. 15, 1992, Pat. No. 5,334,389.

[51] Int. Cl.[6] .................. A01N 59/00; A01N 59/16; A01N 59/20; A01N 59/24; A01N 35/06; B63B 59/04

[52] U.S. Cl. .................. 424/609; 424/78.09; 424/409; 424/630; 424/638; 424/646; 514/245; 514/332; 514/335; 514/372; 514/417; 514/425; 514/476; 514/491; 514/492; 514/493; 514/499; 514/500; 514/501; 514/525; 514/596; 514/600; 514/630; 514/638; 514/646; 514/690; 504/158; 504/161; 114/67 R; 114/222; 114/361; 405/216; 428/907; 428/543; 428/411.1; 106/18.33; 106/15.05; 210/764; 523/122

[58] Field of Search .................. 514/690, 372, 514/245, 332, 335, 417, 425, 476, 491–493, 499, 500, 501, 525, 596, 600, 630, 638, 646; 424/409, 609, 78.09, 630, 638, 646; 114/67 R, 222, 361; 106/18.33, 15.05; 210/764; 523/122; 405/216; 504/158, 161

[56] References Cited

U.S. PATENT DOCUMENTS

| 3,720,711 | 3/1973 | Jirkovsky | 564/191 |
|---|---|---|---|
| 3,761,488 | 9/1973 | Lewis et al. | 548/213 |
| 4,170,631 | 10/1979 | Young et al. | 424/19 |
| 4,286,983 | 9/1981 | Van Gilse et al. | 564/367 |
| 4,410,642 | 10/1983 | Layton | 523/122 |
| 4,504,305 | 3/1985 | Iwataki et al. | 564/27 |
| 4,596,724 | 6/1986 | Lane et al. | 427/385.5 |
| 4,788,302 | 11/1988 | Costlow et al. | 549/458 |
| 4,923,894 | 5/1990 | Kanda et al. | 514/493 |
| 5,128,370 | 7/1992 | Grabley et al. | 514/461 |
| 5,154,747 | 10/1992 | Yokoi et al. | 514/717 |

FOREIGN PATENT DOCUMENTS

| 54-44018A | 4/1979 | Japan . |
| 55-130905 | 10/1980 | Japan . |
| 1519882 | 8/1978 | United Kingdom . |
| 2006183A | 5/1979 | United Kingdom . |

OTHER PUBLICATIONS

D. J. Gerhart et al., *Chemical Ecology and the Search for Marine Antifoulants; Journal of Chemical Ecology* 14 pp. 1905–1917 (1988).

M. A. Sears et al., *Antifouling Agents from Marine Sponge, Journal of Chemical Ecology* 16, pp. 791–799 (1990).

Primary Examiner—Allen J. Robinson
Assistant Examiner—John D. Pak
Attorney, Agent, or Firm—Bell, Seltzer, Park & Gibson

[57] ABSTRACT

A method of controlling the attachment of organisms to an underwater surface is disclosed. The method comprises contacting the organisms with a compound of Formula I

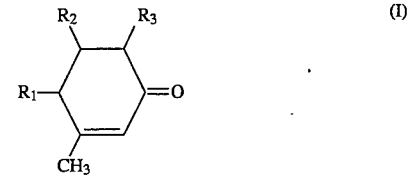

wherein $R_1$, $R_2$ and $R_3$ are each independently hydrogen, $C_1$–$C_3$ alkyl, $C_1$–$C_3$ alkoxy, halogen, or hydroxyl. Antifouling coatings and cementitious compositions containing a compound of Formula I are also disclosed.

12 Claims, 2 Drawing Sheets

ANTIFOULING COATING AND METHOD FOR USING SAME

This application is a divisional of pending prior application Ser. No. 07/961,159, filed Oct. 15, 1992, Allowed Mar. 28, 1994, now U.S. Pat. No. 5,334,389 the disclosure of which is incorporated by reference herein in its entirety.

FIELD OF THE INVENTION

This invention relates generally to coatings used to protect underwater surfaces from settlement by aquatic organisms, and more specifically relates to the inclusion of 3-methyl-2-cyclohexene-1-one or a derivative thereof in such a coating.

BACKGROUND OF THE INVENTION

In marine, brackish, and freshwater environments, organisms collect; settle, attach, and grow on submerged structures. Organisms which do so can include algae, fungi, microbes, and aquatic animals, such as tunicates, hydroids, bivalves, bryozoans, polychaete worms, sponges, and barnacles. Submerged structures can include the underwater surfaces of ships, docks and piers, pilings, heat exchangers, dams, piping structures, such as intake screens, and cooling towers. The presence of these organisms, known as the "fouling" of a structure, can be harmful in many respects. They can add to the weight of the structure, hamper its hydrodynamics, reduce its operating efficiency, increase susceptibility to corrosion, and degrade or even fracture the structure. The common method of controlling the attachment of fouling organisms is by protecting the structure to be protected with a paint or coating which contains an antifouling agent. Exemplary antifouling coatings and paints are described in U.S. Pat. No. 4,596,724 to Lane, U.S. Pat. No. 4,410,642 to Layton, and U.S. Pat. No. 4,788,302 to Costlow. Application of a coating of this type inhibits the attachment, or "settling" of the organism, by either disabling the organism or providing it with an unattractive environment upon which to settle.

Of the fouling organisms noted above, barnacles have proven to be among the most difficult to control. Typically, commercial antifouling coatings and paints include a toxic metal-containing compound such as tri-n-butyl tin (TBT), or cuprous oxide, which leaches from the coating Although these compounds exhibit moderate success in inhibiting barnacle settlement, they degrade slowly in marine environments, and therefore are ecologically harmful. In fact, TBT is sufficiently toxic that its release rate is limited by legislation in some countries.

Some experimental non-toxic compounds have been tested with limited success in barnacle settlement inhibition. See, e.g., Gerhart et al., *J. Chem. Ecol.* 14:1905–1917 (1988), which discloses the use of pukalide, epoxypukalide, and an extract produced by the octocoral *Leptogorgia virgulata*, to inhibit barnacle settlement, and Sears et al., *J. Chem. Ecol.* 16:791–799 (1990), which discloses the use of ethyl acetate extracts of the sponge *Lissodendoryx isodictyalis* to inhibit settlement.

In view of the foregoing, it is a first object of the present invention to provide a non-toxic antifouling compound which effectively inhibits the settlement of barnacles on an underwater surface.

It is a second object of the present invention to provide an antifouling paint or coating which releases the aforementioned antifouling compound.

SUMMARY OF THE INVENTION

These and other objects are satisfied by the present invention, which as a first aspect includes a method of controlling the attachment of organisms to an underwater surface. The method comprises contacting the organisms with a compound of Formula I

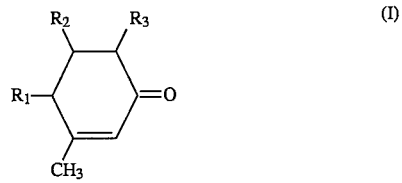

wherein $R_1$, $R_2$ and $R_3$ are each independently hydrogen, $C_1$–$C_3$ alkyl groups, $C_1$–$C_3$ alkoxy groups, halogens, or hydroxyl groups. A second aspect of the present invention is an antifouling coating comprising a compound of Formula I and a film-forming component. This coating may optionally include an additional biocide.

A third aspect of the present invention is an article coated with a coating of the type described above. Exemplary articles include boats and boat hulls, piers and pilings, buoys, offshore oil-rigging equipment and structures, and the like.

A fourth aspect of the present invention is a cementitious composition comprising a compound of Formula I and a cementitious matrix.

DETAILED DESCRIPTION OF THE INVENTION

Figure 1:
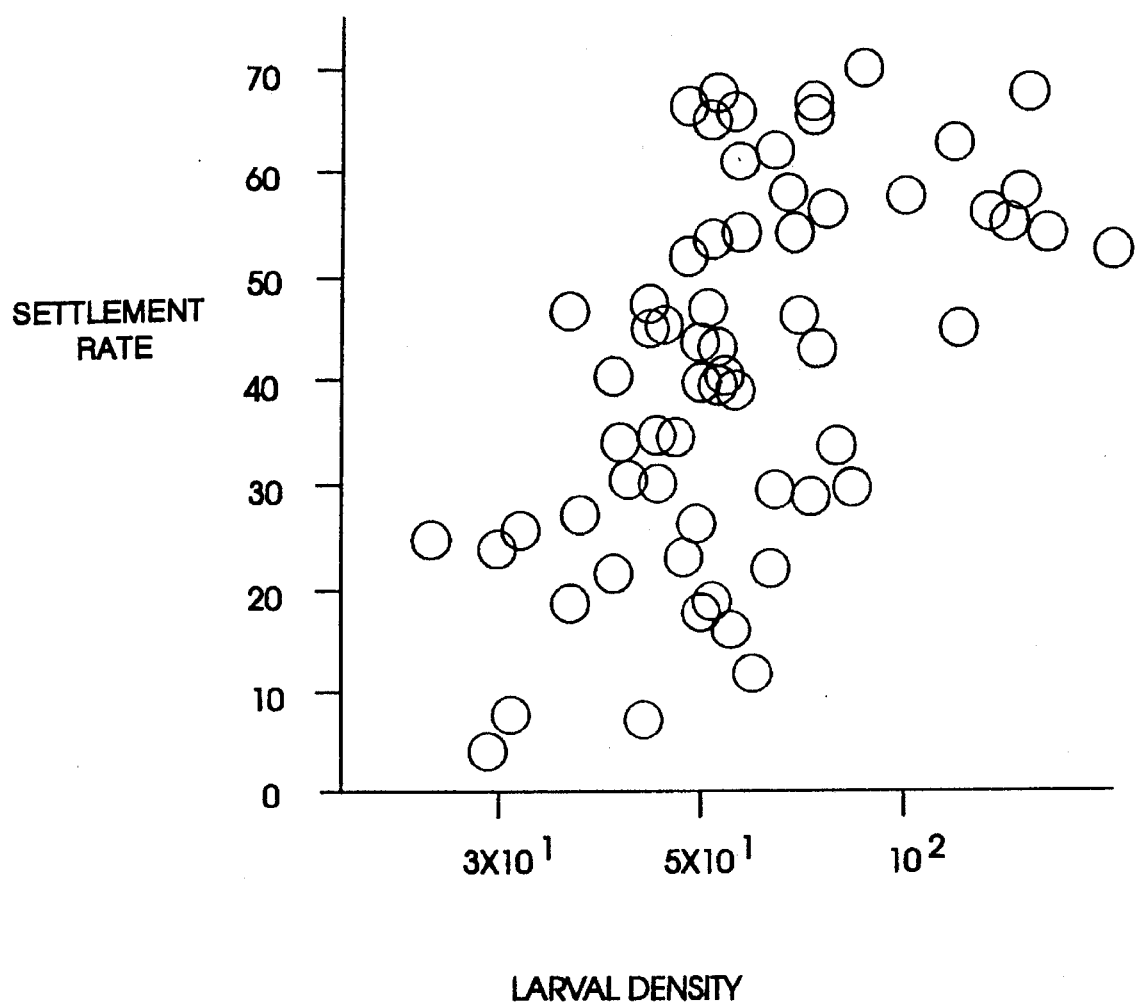
FIG. 1 is a graph plotting settlement rate of untreated controls as a function of larval density. The least squares regression equation for the data is $Y = 47.4(\log X) - 41.3$, where Y represents settlement rate and X represents larval density.

The present invention is directed to controlling the attachment of unwanted organisms to submerged surfaces by contacting the organism with an antifouling compound of Formula I. The antifouling compounds of the present invention include 3-methyl-2-cyclohexene-1-one (MCH) and substituted derivatives thereof as given herein. MCH is a known antiaggregative pheromone for Douglas fir beetles. See e.g., U.S. Pat. No. 4,170,631 to Young et al.

It has been discovered that compounds of Formula I inhibit the aggregation of fouling organisms, particularly barnacles. As used herein, "settlement" refers to the attachment of aquatic organisms to an underwater structure. Thus contacting an organism with a compound of Formula I in the aquatic environment adjacent and in contact with a submerged surface reduces settlement of the organism on that submerged surface.

As noted above, in the compound of Formula I $R_1$, $R_2$ and $R_3$ are each independently selected from the group consisting of hydrogen, $C_1$–$C_3$ alkyl (e.g., methyl, ethyl, propyl), $C_1$–$C_3$ alkoxy (e.g., methoxy, ethoxy, propoxy), halogen (e.g., chloro, bromo, fluoro, iodo), and hydroxy. Preferably, the compound is unsubstituted or is substituted once with a methyl or methoxy group; more preferably, the compound is unsubstituted.

The compounds of Formula I are known and can be made by conventional techniques for synthesizing derivatives of cyclohexanones known to those skilled in this art. See, e.g., U.S. Pat. No. 4,170,631 to Young et al.

In the practice of the method of the present invention, the antifouling compound may be contacted to the organism by coating the object to be protected with a coating containing the antifouling compound, by including the antifouling compound within the material comprising an aquatic article which then releases the compound into the aquatic environment immediately adjacent the external surfaces of the article, by releasing the compound directly into the aquatic environment surrounding the protected object, or by any other method wherein the compound contacts the organism prior to its attachment to the surface. As used herein, the term "contacting" means that an amount of antifouling compound sufficient to inhibit settlement of the organism on the surface of interest physical contacts the organism, whether by direct external contact, inhalation, respiration, digestion, imbibition, or any other process.

The amount of compound to be used in the method will vary depending on a number of factors, including the identity of the antifouling compound, the identity of the organism to be inhibited, and the mode of contact. In addition, the rate at which the compound is released into the surrounding aquatic environment can be a major factor in determining both the effectiveness of the method and the duration of protection. If the compound is released too rapidly, it will be exhausted quickly, and the coating must be re-applied for the surface to be protected. If on the other hand the release rate of the antifouling compound is too slow, the concentration of the compound in the aquatic environment immediately surrounding the surface to be protected may be insufficient to inhibit settlement. Preferably, the antifouling compound is released into the environment adjacent the protected surface at the rate of between about 0.0001 and 1000 $\mu g/cm^2$-hr, and more preferably is released at a rate of between about 0.01 and 100 $\mu g/cm^2$-hr.

The organisms against which a surface can be protected by the present method can be any organism which can attach to a submerged surface. Exemplary organisms include algae, including members of the phyla Chlorophyta and Phaeophyta, fungi, microbes, tunicates, including members of the class Ascidiacea such as *Ciona intestinalis, Diplosoma listerianium*, and *Botryllus sclosseri*, members of the class Hydrozoa, including *Clava squamata, Hydractinia echinata, Obelia geniculata*, and *Tubularia larynx*, bivalves, including *Mytilus edulis, Crassostrea virginica, Ostrea edulis, Ostrea chilensia*, and *Lasaea rubra*, bryozoans, including *Electra pilosa, Bugula neritina*, and *Bowerbankia gracilis*, polychaete worms, including *Hydroides norvegica*, sponges, and members of the class Cirripedia (barnacles), such as *Balanus amphitrite, Lepas anatifera, Balanus balanus, Balanus balanoides, Balanus hameri, Balanus crenatus, Balanus improvisus, Balanus galeatus*, and *Balanus eburneus*. Specific fouling organisms to which the invention is directed include barnacles, In a preferred embodiment of the method, barnacles are prevented from settling on a structure.

In addition to the compound of Formula I, the method may further comprise contacting fouling organisms with other antifouling agents which may act in combination or synergistically with the compound of Formula I. Exemplary antifouling agents include: manganese ethylene bisdithiocarbamate, a coordination product of zinc ion and manganese ethylene bisdithiocarbamate; zinc ethylene bisdithiocarbamate; zinc dimethyl dithiocarbamate, 2,4,5,6-tetrachloroisophthalonitrile; 2-methylthio-4-t-butylamino-6-cyclopropylamino-S-triazine; 3-(3,4-dichlorophenyl)-1,1-dimethyl urea; N-(fluorodichloromethylthio)-phthalimide; N,N-dimethyl-N'-phenyl-(N-fluorodichloromethylthio)-sulfamide; tetramethylthiuram disulfide; 2,4,6-trichlorophenyl maleimide; zinc 2-pyridinthiol-1-oxide; copper thiocyanate; Cu-10% Ni alloy solid solution; and 4,5-dichloro-2-n-octyl-4-isothiazolin-3-one.

The invention includes as a second aspect an antifouling coating which comprises a compound of Formula I and a film-forming component. The compound of Formula I is defined as described above. The film-forming component of a coating of the present invention can be any component or combination of components which is applied easily to the surface to be protected, adheres to the submerged surface to be protected, and permits the release of the antifouling compound into the water immediately surrounding the coated surface. Clearly, different film-forming components will be preferred depending on the material comprising the underwater surface, the operation requirements of the surface, the configuration of the surface, and the antifouling compound. Exemplary film-forming components include polymer resin solutions and aqueous powder solutions, with polymer resin solutions being preferred. Exemplary polymer resins include unsaturated polyester resins formed from (a) unsaturated acids and anhydrides, such as maleic anhydride, fumaric acid, and itaconic acid; (b) saturated acids and anhydrides, such as phthalic anhydride, isophthalic anhydride, terephthalic anhydride, tetrahydrophthalic anhydride, tetrahalophthalic anhydrides, chlorendic acid, adipic acid, and sebacic acid; (c) glycols, such as ethylene glycol, 1,2 propylene glycol, dibromoneopentyl glycol, DIANOL 33®, and DIANOL 22®; and (d) vinyl monomers, such as styrene, vinyl toluene, chlorostyrene, bromostyrene, methylmethacrylate, and ethylene glycol dimethacrylate. Other suitable resins include vinyl ester-, vinyl acetate-, and vinyl chloride-based resins, and urethane-based resins.

The percentage of the antifouling compound of Formula I in the coating required for proper release of the compound into the aquatic environment surrounding the surface to be protected will vary depending on the identity of the antifouling compound, the identity of the film-forming component of the coating and other additives present in the coating which may affect release rate. The release rate of the antifouling compound can be a major factor in determining both the effectiveness of the method and the duration of protection. If the compound is released too rapidly, it will be exhausted quickly, and the coating must be re-applied for the surface to be protected. If on the other hand the release rate of the antifouling compound is too slow, the concentration of the compound in the aquatic environment immediately surrounding the surface to be protected may be insufficient to inhibit settlement. Thus a coating with a rapid release rate should include a relatively high percentage of the antifouling compound so that protection of the submerged surface continues for a suitable duration. It is preferred that the coating be released into the surrounding water at a rate of between about 0.0001 and 1,000 $\mu g/cm^2$-hr to inhibit settlement of barnacles; more preferably, the compound will comprise between about 0.01 and 100 $\mu g/cm^2$-hr. Preferably, the antifouling compound comprises between about 0.001 and 80 percent of the coating by weight, and more preferably comprises between 0.01 and 20 percent of the coating.

Those skilled in this art will appreciate that a coating of the present invention can comprise any number of forms, including a paint, a gelcoat, a varnish, and the like. The coating can include components in addition to the antifouling coating and film-forming component which confer a desirable property, such as hardness, strength, rigidity, reduced drag, impermeability, or water resistance.

The present invention encompasses any article which contains a surface coated with a coating containing a compound of Formula I. Those articles which are particularly suitable for protection with the coating are those which, either intentionally or inadvertently, are submerged for at least the duration required for an organism to settle on a submerged object. Coated articles can comprise any material to which aquatic organisms are known to attach, such as metal, wood, concrete, polymer, and stone. Exemplary articles which may require antifouling protection include boats and boat hulls, fishing nets, fish cages, recreational equipment, such as surfboards, jet skis, and water skis, piers and pilings, buoys, off-shore oil rigging equipment, and decorative or functional stone formations.

The present invention also includes a cementitious composition which includes an antifouling compound of Formula I and a cementitious matrix. Such a composition is suitable for use in submerged structures such as piers, pilings, and offshore oil rigging equipment and scaffolding, upon which fouling organisms tend to settle. Exemplary cementitious matrix compositions include portland cement and calcium aluminate based compositions. As those skilled in this art will appreciate, the cementitious matrix should be able to release the antifouling compound, and the antifouling compound must be present in sufficient concentration that the release rate of the compound into the surrounding aquatic environment inhibits settling of organisms on the submerged surface of an article formed from the composition. It is preferred that the antifouling compound be present in such a composition at a concentration by weight of between 0.001 and 30 percent.

The invention is now described in more detail in the following non-limiting examples. These examples are provided to more completely disclose the information to those skilled in this art, and are not intended to be construed as limiting on the invention.

EXAMPLE 1

Settlement Assay Procedure

Laboratory experiments were performed with day 3 cyprid larvae of the acorn barnacle Balanus amphitrite cultured as described in Rittschof et al., *J. Exp. Marine Biol. & Ecol.* 82:131–146 (1984). Settlement experiments were performed using polystyrene dishes as described in Rittschof et al., *J. Chem. Ecol.* 11:551–563 (1985) and in Sears et al., *J. Chem. Ecol.* 16:791–799 (1990). Larvae were added to polystyrene dishes containing 5 ml of aged seawater that had been passed through a 100 kilo-Dalton cut-off filter and varying levels of 3-methyl-2-cyclohexene-1-one. Controls consisted of barnacle larvae and filtered seawater added to polystyrene dishes without 3-methyl- 2-cyclohexene-1-one. After addition of larvae, the dishes were incubated for 20 to 24 hours at 28° C. on a 15:9 light:dark cycle.

The dishes were then removed from the incubator, examined under a dissecting microscope to determine if larvae were living (moving) or dead (not moving). Larvae were then killed by addition of several drops of 10% formalin solution.

Settlement rate was quantified as number of larvae that had attached to the dish surface, expressed as a percentage of total larvae in the dish. Dishes were more than 200 larvae were excluded from subsequent analysis, since extremely high larval densities may inhibit settlement rates. Linear regressions were performed using percentage settlement as the dependent (Y) variable and log of larval density (larvae per dish) as the independent variable. Each dish was treated as a single replicate.

EXAMPLE 2

Settlement Assay Results

Figure 2:
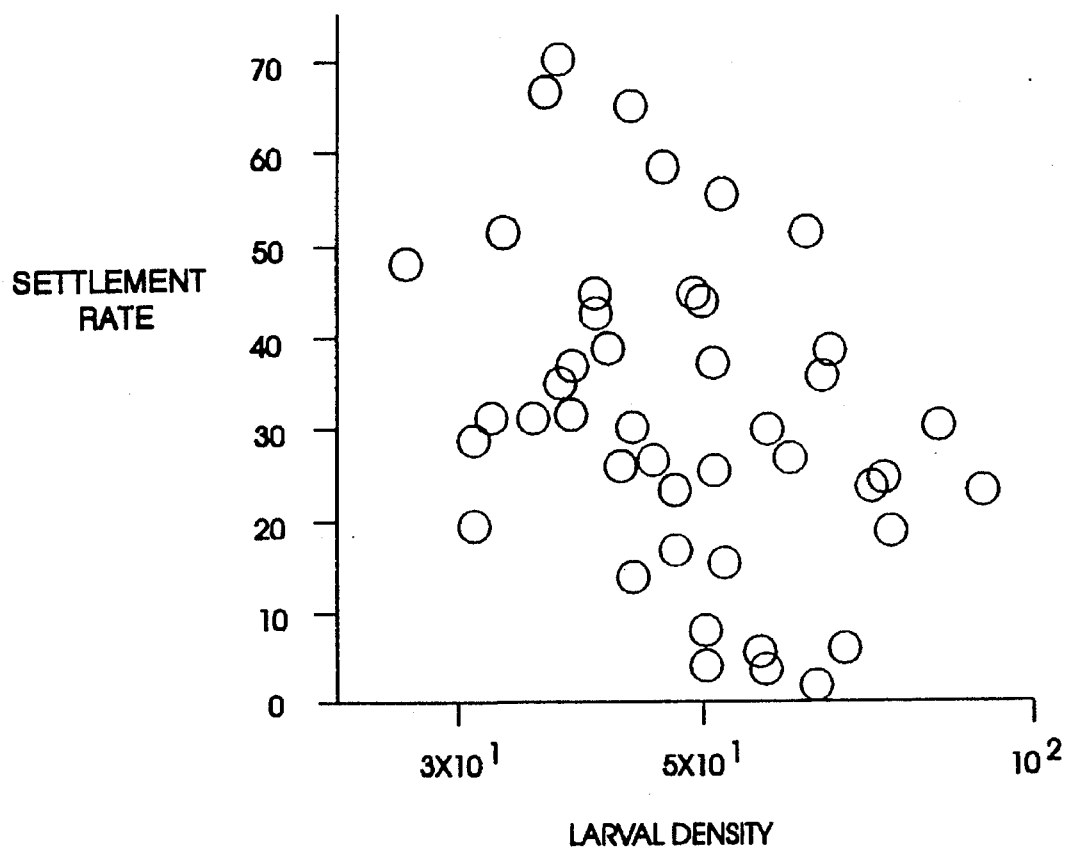
FIG. 2 is a graph plotting settlement rate of treated samples as a function of larval density. The least squares regression equation for the data is $Y = -51.7(\log X) + 118.6$, where Y represents settlement rate and X represents larval density).

Data were combined for all control dishes (n=65 for combined data set). In the controls, barnacle settlement increased as a linear function of larval density (FIG. 1) The least squares regression equation for the data is: $Y=47.4(\log X)-41.3$, where Y represents settlement rate and X represents larval density. Data also were combined for treatments generated by addition of 3-methyl-2-cyclohexene-1-one at concentrations of 9, 90, and 900 picomolar (n=44 for combined data set). At these concentration, barnacle settlement decreased as a linear function of barnacle density (FIG. 2). The least squares regression equation for this data set is: $Y=-51.7(\log X)+118.6$, where Y represents settlement rate and X represents larval density).

Data also were combined for all higher concentrations of 3-methyl-2-cyclohexene-1-one (n=107 for combined data set—data not shown). The regression line for these replicates was not significantly different from that of the untreated controls (regression equation: $Y=48.5(\log X)-49.1$, where Y represents settlement rate and X represents larval density). The decrease in effectiveness at higher concentrations is not atypical for antiaggregative pheromones.

The foregoing examples are illustrative of the present invention, and are not to be construed as limiting thereof. The invention is defined by the following claims, with equivalents of the claims to be included therein.

That which is claimed is:

1. An article having an underwater surface to which is bonded a coating which coating controls the attachment of barnacles to that surface, said coating comprising:

(a) a compound of Formula I:

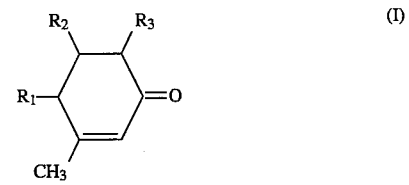

wherein $R_1$, $R_2$ and $R_3$ are each independently hydrogen, $C_1$–$C_3$ alkyl, $C_1$–$C_3$ alkoxy, halogen, or hydroxyl groups in an amount effective to control the attachment of barnacles to said surface; and (b) a film-forming component.

2. An article according to claim 1, wherein said article is a boat.

3. An article according to claim 1, wherein said article is a pier.

4. An article according to claim 1, wherein said compound comprises between about 0.0001 and 80 percent by weight.

5. An article according to claim 1, wherein said coating is a paint.

6. An article according to claim 1, wherein said coating includes an additional antifouling compound.

7. An article according to claim 6, wherein said additional antifouling compound is selected from the group consisting of: manganese ethylene bisdithiocarbamate, zinc ethylene bisdithiocarbamate, zinc dimethyl dithiocarbamate, 2,4,5,6-tetrachloroisophthalonitrile, 2-methylthio-4-t-butylamino-6-cyclopropylamino-S-triazine, 3-(3,4-dichlorophenyl)-1,1-dimethyl urea, N-(fluorodichloromethylthio)-phthalimide, N,N-dimethyl-N'-phenyl-(N-fluorodichloromethylthio)-sulfamide, tetramethylthiuram disulfide, 2,4,6-trichlorophenyl maleimide, zinc 2-pyridinthiol-1-oxide, copper thiocyanate, Cu-10% Ni alloy solid solution, and 4,5-dichloro-2-n-octyl-4-isothiazolin-3-one.

8. A method of combatting the attachment of barnacles to an article having an underwater surface comprising;

(a) coating the underwater surface with a composition containing a compound of Formula I:

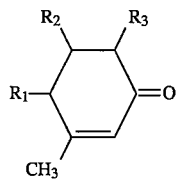

wherein $R_1$, $R_2$ and $R_3$ are each independently hydrogen, $C_1$–$C_3$ alkyl, $C_1$–$C_3$ alkoxy, halogen, or hydroxyl groups, in an amount effective to control the attachment of barnacles to said surface; and then (b) contacting said barnacles with a compound of Formula I.

9. A method article according to claim 8, wherein said compound comprises between about 0.0001 and 80 percent by weight of said composition.

10. A method according to claim 8, wherein said composition is a paint.

11. A method according to claim 8, wherein said composition includes an additional antifouling compound.

12. A method according to claim 11, wherein said additional antifouling compound is selected from the group consisting of: manganese ethylene bisdithiocarbamate, zinc ethylene bisdithiocarbamate, zinc dimethyl dithiocarbamate, 2,4,5,6-tetrachloroisophthalonitrile, 2-methylthio-4-t-butylamino-6-cyclopropylamino-S-triazine, 3-(3,4-dichlorophenyl)-1,1-dimethyl urea, N-(fluorodichloromethylthio)-phthalimide, N,N-dimethyl-N'-phenyl-(N-fluorodichloromethylthio)-sulfamide, tetramethylthiuram disulfide, 2,4,6-trichlorophenyl maleimide, zinc 2-pyridinthiol-1-oxide, copper thiocyanate, Cu-10% Ni alloy solid solution, and 4,5-dichloro-2-n-octyl-4-isothiazolin-3-one.

* * * * *